United States Patent [19]

Waysenson

[11] Patent Number: 5,006,065
[45] Date of Patent: Apr. 9, 1991

[54] DENTAL ARTICULATOR

[76] Inventor: Bernard Waysenson, 55, Allees Jean-Jaures, 31000 Toulouse, France

[21] Appl. No.: 395,263

[22] Filed: Aug. 17, 1989

[30] Foreign Application Priority Data

Feb. 17, 1988 [FR] France .................. 88 02262

[51] Int. Cl.⁵ ............................................. A61C 11/00
[52] U.S. Cl. ......................................... 433/63; 433/54
[58] Field of Search ...................... 433/54, 61, 68, 65, 433/63, 69

[56] References Cited

U.S. PATENT DOCUMENTS

| 4,265,620 | 5/1981 | Moro et al. | 433/54 |
| 4,330,276 | 5/1982 | Becker et al. | 433/69 |
| 4,468,198 | 8/1984 | Kataoka et al. | 433/54 |

Primary Examiner—Cary E. Stone
Attorney, Agent, or Firm—Hill, Van Santen, Steadman & Simpson

[57] ABSTRACT

A dental articulator incorporates members which are models of the patient's upper jaw and mandible, and incorporates six servo motors connected to the mandible member, for movement of the same about three orthogonal translation axes, and three orthogonal axes of rotation.

4 Claims, 4 Drawing Sheets

DENTAL ARTICULATOR

The present invention relates to a dental articulator, and more particularly to a robotic dental articulator capable of executing the entire range of movements of a patient's lower jaw or mandible.

BACKGROUND OF THE INVENTION

In the past, for the study of mandibular motion of a patient, articulators which have been available are extremely limited in accuracy and versatility. Such articulators are not able to reproduce the entire range and motion of movement of a patient's jaw, or to simulate the actual speed of such motion, or to faithfully reproduce the path of motion from a rest position to a position of extension in several different directions, or to reproduce a path between different extended positions.

It is desirable to provide a robotic articulator capable of improved accuracy, and to provide a more realistic simulation, in order to allow the study of mandibular motion, such as that involved in bruxism, for example, to facilitate diagnosis of disfuction, and to aid in design and construction of bridge work or other prosthetic appliances.

SUMMARY OF THE INVENTION

It is a principal object of the invention to provide a robotic dental articulator capable of executing the entire range of movements of a patient's mandible.

Another object of the present invention is to provide such an articulator, capable of six degrees of freedom, so that the patient's actual mandibular motion can be reproduced.

In accordance with the present invention, a robotic articulator is provided having six degrees of freedom, with three possible translations about orthogonal axes, and rotations about three orthogonal axes.

BRIEF DESCRIPTION OF THE DRAWINGS

Reference will now be made to the accompanying drawings, in which.

DESCRIPTION OF THE PREFERRED EMBODIMENTS

Figure 1:
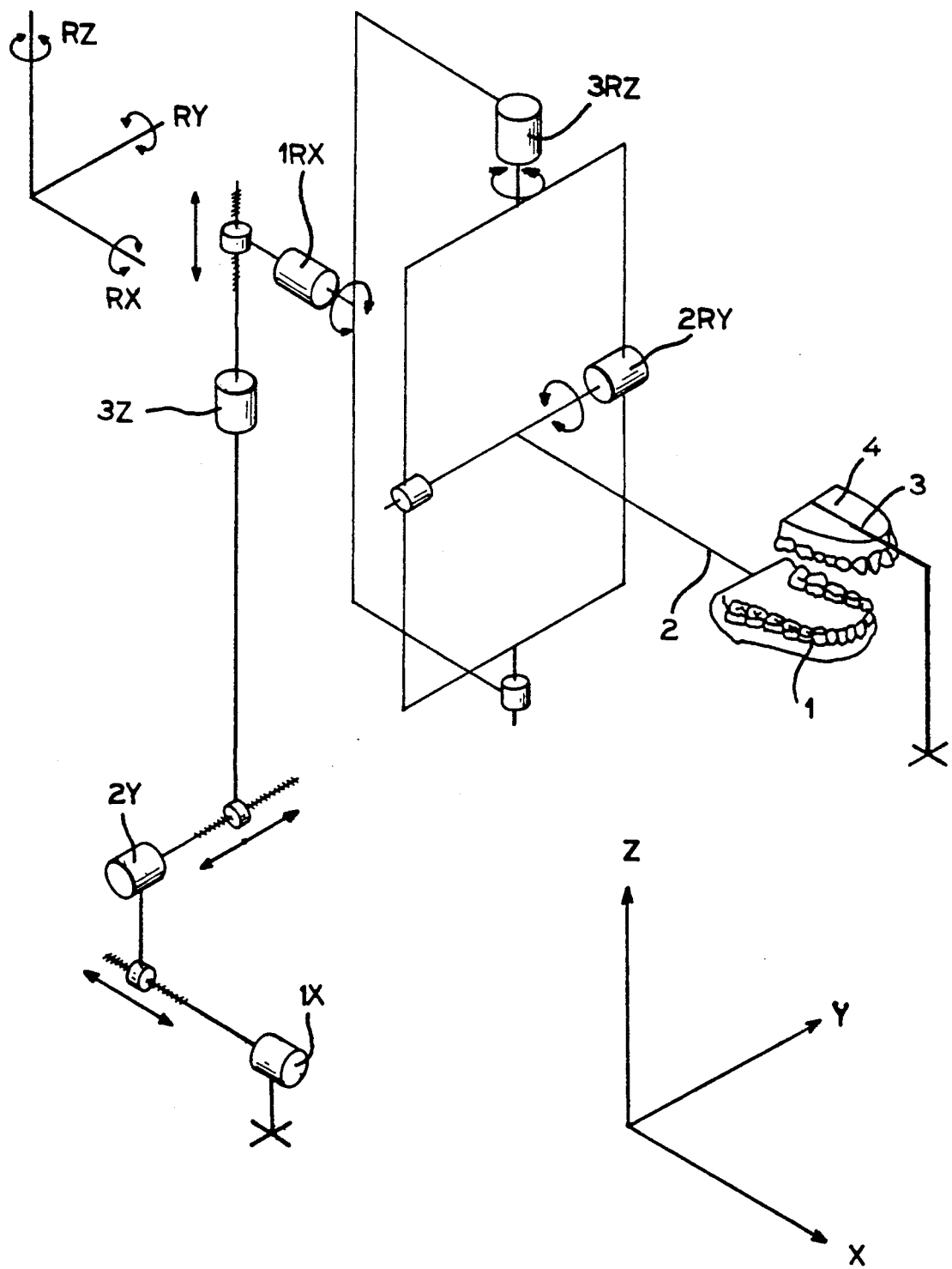
FIG. 1 is a diagrammatic view of an articulator incorporating an illustrative embodiment of the invention, with three orthogonal axes, with means for imparting translation and rotation with respect to each axis.

Referring now to FIG. 1, an articulator incorporating an illustrative embodiment of the present invention is illustrated. The model of the patient's lower jaw or mandible 1 is fixed to a rod 2 which extends rearwardly in a generally horizontal direction from the mandible 1. The model of the patient's upper jaw and teeth 4 is supported in a fixed position by means of a support 3. The rest of the structure illustrated in FIG. 1 is designed to impart motion to the rod 2 in six degrees of freedom, to simulate the entire range of motion of the mandible model 1 relative to the upper jaw 4.

The rear end of the rod 2 is connected to a shaft aligned with the horizontal axis of a rotator 2RY, extending between the rotator and a bearing. Rotation of the rotator 2RY moves the rod 2 and the mandible 1 about a horizontal axis of rotation, to impart a rotation about a pitch axis to the mandible 1.

The rotator 2RY, and its corresponding bearing, are mounted on a rectangular frame, which is adapted for rotation about a vertical axis by means of rotator 3RZ, which is provided with a corresponding bearing at the other end of the frame. Rotation of the rotator 3RZ imparts a rotation to the mandible 1 about a yaw axis.

A frame connects the rotator 3RZ and its corresponding bearing with the axis of a third rotator 1RX, which axis is aligned with the rod 2. Rotation of the rotator 1RX imparts rotation to the rod 2 and mandible 1 about a roll axis.

The rear extension of the rod upon which the rotator 1RX is mounted is secured to a nut, threaded onto a screw which is turned by a rotator 3Z. Operation of the rotator 3Z turns the screw within the nut, and causes a raising or lowering of the entire assembly from the rotator 1RX through the rod 2 and the mandible 1. This imparts an up and down rectilinear motion to the mandible 1. The actuator 3RZ is mounted on a nut which is threaded on a screw turned by a second actuator 2Y. Operation of the actuator 2Y turns the screw, to cause the nut, the actuator 3RZ, and any other components through the rod 2 and the mandible 1 to move rectilinearly in the Y direction, from side to side relative to the upper jaw 4. The actuator 2Y is in turn mounted on a nut threaded on a screw turned by an actuator 1X, so that rotation of the screw by the actuator 1X moves the entire assembly, including the mandible 1 in the X direction. The apparatus therefore exhibits six degrees of freedom, including three translations in three orthogonal directions, and three rotations about the three orthogonal axes. The rotations are identified as RX, RY and RZ, and correspond to the operation of the rotators 1RX, 2RY and 3RZ. The translations are along the X, Y and Z axes, and correspond to operation of the 1X, 2Y and 3Z actuators.

Figure 2:
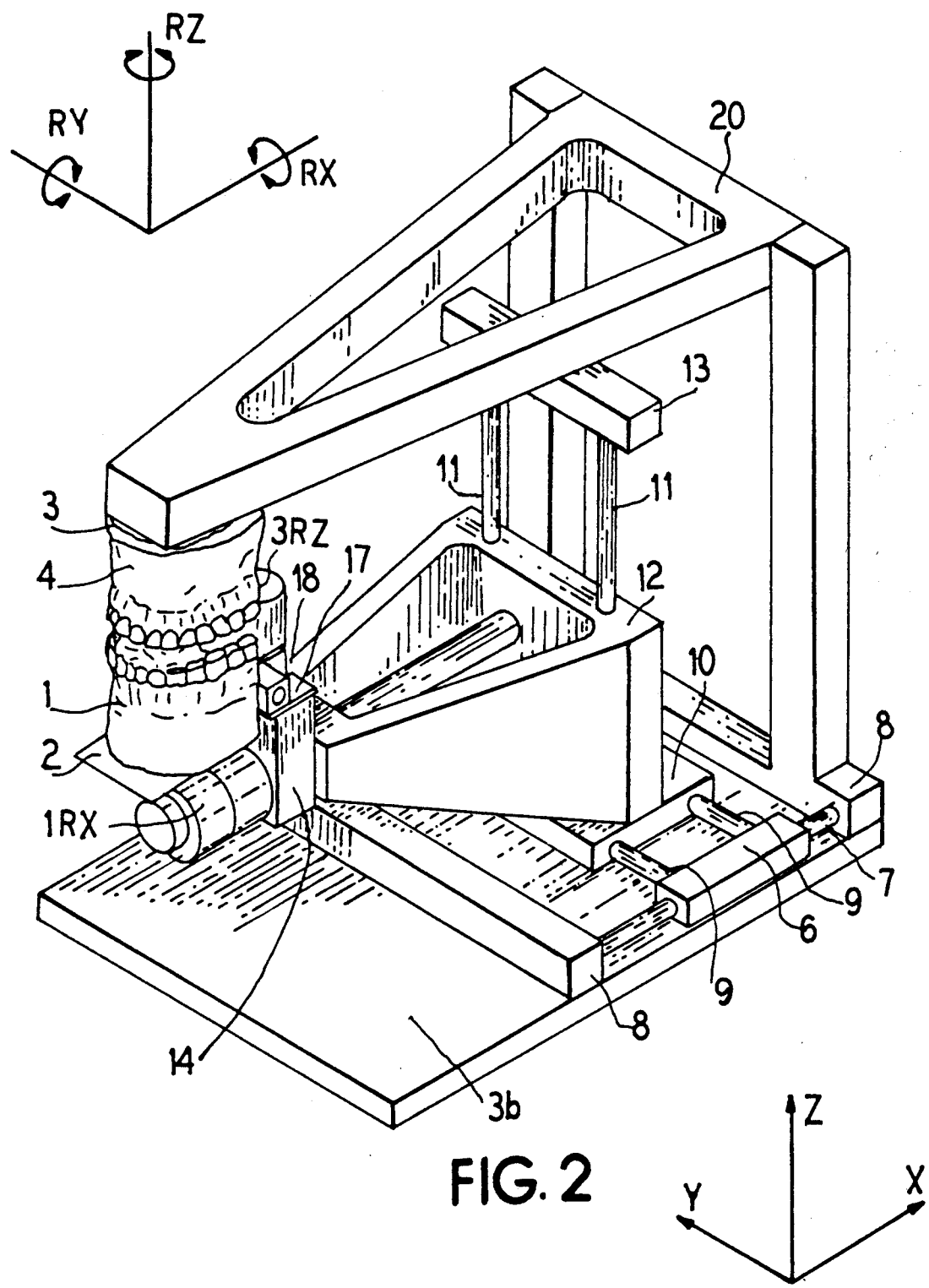
FIG. 2 is a perspective view of apparatus incorporating the present invention.

FIG. 2 is a perspective view of a physical assembly carrying out the three translations and three rotations described in connection with FIG. 1. The mandible 1 is mounted on a support or shelf 2, which substitutes for the rod 2 illustrated in FIG. 1. A model 4 of the patient's upper jaw is connected in fixed relationship mounted on a frame 20 having a base 3B which may be supported on a convenient horizontal surface. A pair of blocks 8 support a guide 7, and a carriage 6 is slidable on the guide 7, so that it can move forwardly and rearwardly relative to the frame ( in the x direction). The carriage supports a pair of guides 9, which extend in the y direction from the carriage 6. A second carriage 10 is slidably mounted on the guides 9, so that it can move left and right on the guides.

A pair of vertical guides 11 are journalled in the block 11 at their bottom ends, and in a block 13 at their upper ends.

A third carriage or yoke 12 is slidably mounted on the guides 11, so that it can be raised and lowered, in the z dirction. Accordingly, by selective energization of the actuators 1X, 2Y and 3Z (FIG. 1), which are omitted from FIG. 2 in the interest of clarity, the yoke 12 can be moved by translation in three degrees of freedom corresponding to the X, Y, Z orthogonal directions. At the front end of the yoke 12, the rotator 1RX is mounted, on a shaft 15 (FIG. 3) which has one end adapted for rotation by the rotator 1RX, and the other end fixed to the yoke 12. A block 14 is fixed to the housing of the rotator 1RX, so that it is adapted for rotation about the shaft 15, in accordance with actuation of the rotator 1RX.

A shaft 16 extends upwardly from the block 14, through a bearing 16A, and a vertical aperture in a yoke 17, and is axially aligned with the rotary shaft of a rotator 3RZ. The housing of the rotator 3RZ is fastened to the yoke 17, so that operation of the rotator 3RZ functions to turn the yoke 17 about the shaft 16.

The yoke 17 has a pair of aligned apertures to receive a shaft 18 of rotator 2RY, the housing of which is fixed to the yoke 17, so that actuation of the rotator 2RY serves to rotate the shaft 18. The platform or shelf 2 is fixed to the shaft 18, and a pair of bearings 18A and 18B allow free rotation of the shelf 2 relative to the yoke 17. Accordingly, the apparatus illustrated in FIG. 3 superimposes three degrees of freedom, namely rotations about the X, Y and Z axes, on the orthogonal translation controled by the actuators 1X, 2Y, and 3Z, and the yoke 12 is adapted for movement in six degrees of freedom, with three orthogonal translation movements, and three orthogonal rotations. Although the actuators 1X, 2Y and 3Z (of FIG. 1) are not explicitly shown in FIG. 2, it will be appreciated by those skilled in the art that the first, second and third carriages 6, 10 and 12, may all be moved by means of the drive screw and nut arrangements illustrated in FIG. 1. The screws may be caused to rotate by means of one or more electric motors or the like, either connected directly to the respective screws, or coupled thereto by means of gears, belts or the like.

It will be appreciated that the model of the patient's mandible 1 illustrated in FIG. 1, can thereby be moved freely relative to the fixed upper jaw 4, by appropriately energizing the various actuators and/or rotators, to cause the mandible 1 to describe the entire range of motions, relative to the upper jaw 4, that may be experienced with a particular patient. In addition, when the motion of the various actuators and rotators is synchronized, then the path taken by the mandible model 1 from a first position to a second position, relative to the fixed upper jaw model 4, can accurately reflect the actual motion experienced by the patient. Since this motion is clearly observable from all angles, using the articulator of the present invention, the motion can be studied more clearly than by merely examining the patient, since the patient's head blocks a number of angles of view of the mandible 1 and its associated upper jaw 4, which may best illustrate the cooperative relationship of the patient's upper and lower jaws.

Figure 3:
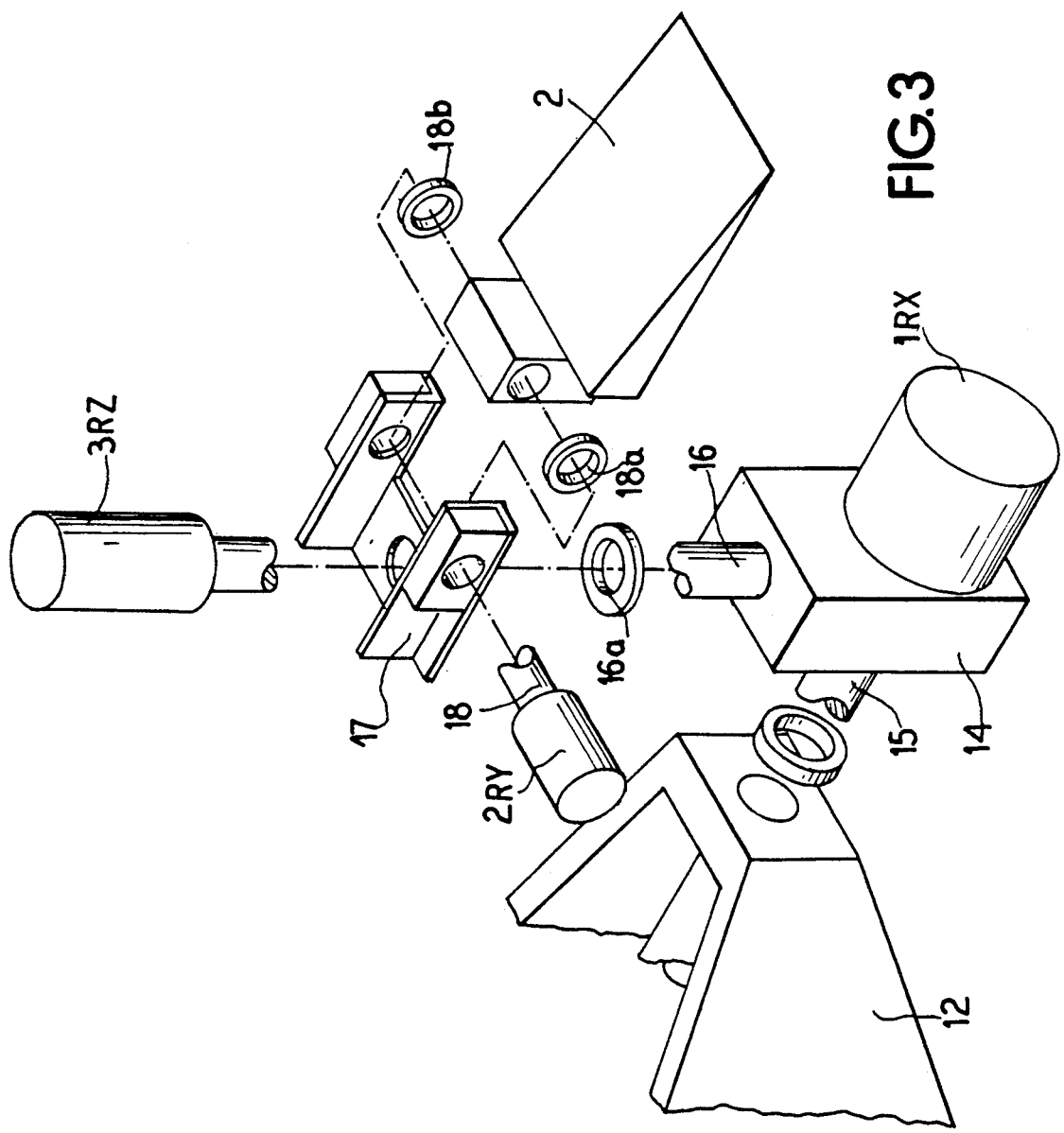
FIG. 3 is an exploded view of a portion of the apparatus illustrated in FIG. 2.
Figure 4:
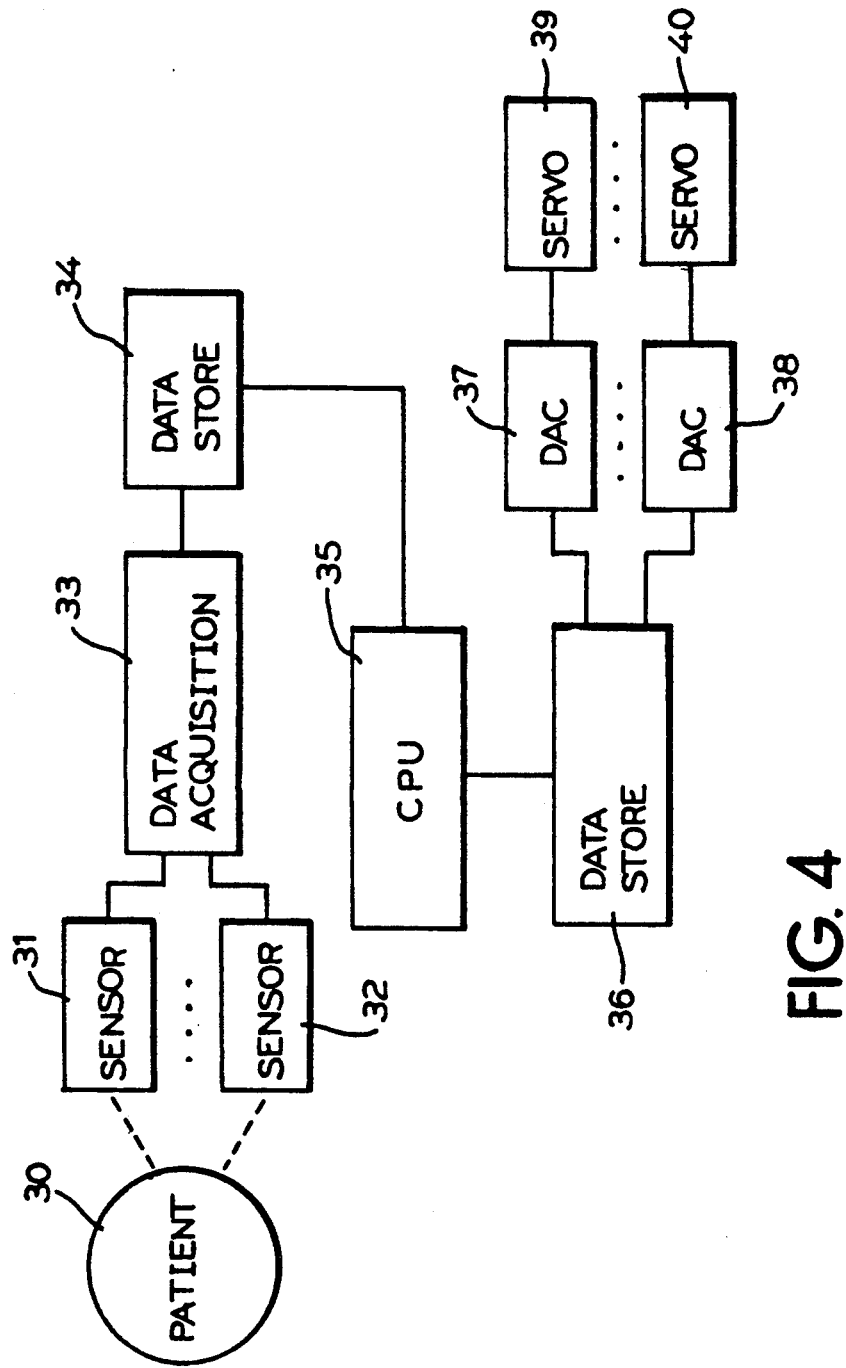
FIG. 4 is a functional block diagram of systems employed in the use of the articulator of the present invention.

Referring to FIG. 4, an entire articulator system is illustrated in diagrammatic form, by which the synchronized signals for driving the various actuators and rotators may be obtained and utilized. The actuators and rotators are indicated in FIG. 3 by the servo motors 39 and 40, only two of which are shown in the interest of simplicity. The signals for driving the motors are supplied through digital-to-analog converters 37 and 38 which receive signals from a digital data store 36. A central processing unit 35, which may incorporate, for example, a microcomputer, causes the data store 36 to read out individual data values to the several digital-to-analog converters 37-38, so that the various servo motors 39-40 can be operated synchronously, so as to cause the appropriate motion of the mandible 1 model relative to the upper jaw model 4. Only two of the six servo motors are illustrated in FIG. 4, for clarity. It will be appreciated that the other four are connected to the CPU via individual DAC's in the same manner as illustrated. The central processing unit 35 may, if desired, cause the data store to emit signals corresponding to a single position of the mandible, corresponding to three specific translations and three specific rotations from a reference position. In this way, a particular position of the mandible model may be achieved and maintained, to permit its examination and study. Alternatively, the central processing unit may cause the data store to produce a series of consecutive output signals to each of the servo motors, moving the mandible model trough a series of positions corresponding to a predetermined movement thereof by the patient of his mandible. This may be, for example, straight line movement from one position and attitude defined by the six coordinates of translation and rotation, to a second such position, either in a straight line interconnecting the two positions, or along a curved path connecting the two positions. Alternatively, the central processing unit may cause the data stored to emit signals corresponding to a particular path through a series of positions, which path has been determined by observation of the patient.

The data stored in the data store unit 36 may be collected by any convenient means. One means of gathering the data is illustrated in FIG. 4. A number of sensors 31-32 are mechanically connected to the patient 30, and furnish signals corresponding to movement of the patient's mandible in six degrees of freedom. For this purpose, six or more sensors 31-32 may be employed, arranged to detect movement of the patient's jaw in three translation directions, and three angular rotations. This data is acquired by a data acquisition unit 33, to which the output of the sensors 31-32 are connected, the data acquisition unit preferably incorporating a multiplexer or the like, whereby the outputs of each of the sensors 31-32 may be interrogated in turn, with the individual data from each sensor stored in the data store 34. The multiplexing is sufficiently rapid so that the several signals acquired from the sensors 31-32 and stored in the data store 34 are essentially simultaneous, corresponding to points, described in six dimensions, as the patient's jaw moves from reference position, to a position of forward extension, left or right extension, etc.

Alternatively, instead of employing physical sensors like the sensors 31 and 32, the patient's movement of his mandible may be observed optically, using two or more video cameras, for example, and the data needed by the data store may be taken from the observed positions of specific points on the patients's mandible, in corresponding frames simultaneously recorded by all of the video cameras.

It will be appreciated that the data stored in the data store unit 34 may be in a different form from that required in the data store unit 36 in order to drive the servo motors 39-40. For example, the sensors may directly measure, for example, the X, Y and Z positions of three fixed points on the patient's mandible, in orthogonal coordinates, or may alternatively measure the distances and angles for such fixed points in spherical coordinates, for example. However, as long as six degrees of freedom are measured, routine calculations may be carried on by the CPU unit 35 in order to translate the acquired data into three translations and three rotations corresponding to a given point in the path of movement in the patient's jaw. The data corresponding to each point is thereby translated from the form which is stored in the data store unit 34, into the form which it is required in the data store unit 36 for driving the servo motors 39-40. Of course, if the data is collected by sensors which directly reflect the translation of the patient's mandible in three directions, and rotation about three axes, then no such translation is required, and the data can be stored directly in the store unit 36.

It will be understood that the process of converting the data involves the use of analytic geometry techniques, which are well known to those skilled in the art, and so they need not be described in detail herein. In addition, it will be appreciated that various servo techniques may be used in connection with the driving of the motors servo 39-40, 40, including, for example, feedback techniques to regulate the speed and position of the servo motors during their operation. It is also contemplated that the servo motors 39-40 may be stepping motors, or the like, whereby the position of each of the motor shafts is determined directly by the number of actuating pulses, or cycles of actuating signals, which are supplied to each respective motor. This is readily determined by calculating the difference in each of the six coordinates between one point on the path of the mandible and the next successive point to be represented, and supplying a number of pulses to each servo motor corresponding to that difference. When pulses are supplied to each of the servo motors in evenly spaced relationship, then the motion of the mandible appears to be continuous, from point to point. Speeding up or slowing down the pulse repetition rate of the pulses applied to each of the motors, by a proportional amount, effects an increase or decrease in the speed of the motion of the mandible, without affecting the path of movement.

It will be apparent from the foregoing that the present invention offers a convenient mechanism for accurately reproducing movement of a patent's mandible for studying such motion, without subjecting the patient to any discomfort, and without impeding the ability of an investigator to inspect or evaluate the motion, at a variety of speeds, including speeds faster and slower than the movement of the patient during the data collection. In addition, the evaluation may take place by trained personnel who need not be present in the dentist's office at the time the data is collected by the sensors 31-32. The articulator of the present invention is capable of accuracies on the order of 0.1 degree in rotation, and 0.1 mm in translation, using commercially available equipment for the servo motors which perform the functions of rotators and actuators.

The arrangement illustrated in FIGS. 1 and 3 of the drawings, which provides rotations about three orthogonal axes passing through a single point, may be referred to as a Cardan set up.

It will be apparent that various modifications and additions may be made in the apparatus of the present invention, without departing from the central features of novelty thereof, which are intended to be defined and secured by the appended claims.

What is claimed is:

1. A dental articulator for reproducing the motion of a patient's mandible, comprising
    a member corresponding to a model of the patient'upper jaw,
    a mandible member corresponding to a model of the patient's mandible, and movement means connected to said mandible member allowing six degrees of freedom of motion of the said mandible member relative to said upper jaw member,
    said movement means comprising six servo motors, each of said servo motors being connected to said mandible member for executing a single translation or rotation relative thereto, said servo motors comprising a first servo motor for movement along a first axis of translation, a second servo motor for movement along a second axis of translation, a third servo motor for movement along a third axis of translation, a fourth servo motor for movement about a first axis of rotation, a fifth servo motor for movement about a second axis of rotation, and a sixth servo motor for movement about a third axis of rotation,
    wherein said three axes of translation are orthogonal, and said three axes of rotation are orthogonal.

2. A dental articulator for reproducing the motion of a patient's mandible, comprising
    a member corresponding to a model of the patient's upper jaw,
    a mandible member corresponding to a model of the patient's mandible, and movement means connected to said mandible member allowing six degrees of freedom of motion of the said mandible member relative to said upper jaw member,
    said movement means comprising six servo motors, each of said servo motors being connected to said mandible member for executing a single translation or rotation relative thereto, said servo motors comprising a first servo motor for movement along a first axis of translation, a second servo motor for movement along a second axis of translation, a third servo motor for movement along a third axis of translation, a fourth servo motor for movement about a first axis of rotation, a fifth servo motor for movement about a second axis of rotation, and a sixth servo motor for movement about a third axis of rotation,
    each of said servo motors being solely responsible for a translation or a rotation, said first servo motor being fixed to a base, for executing movement relative to said base, said second servo motor being fixed to a member moved by said first servo motor, and each successive servo motor being fixed to a member moved by the previous servo motor, with said sixth servo motor adapted to directly support said mandible member.

3. Apparatus according to claim 2, wherein said first and second servo motors execute translations in the orthogonal X and Y directions, said third servo motor executes a translation of the vertical direction, and said fourth, fifth and sixth servo motors, mounted according to a Cardan set up, execute rotations about the X, Y and Z axes, respectively.

4. A dental articulator for reproducing the motion of a patient's mandible, comprising
    a member corresponding to a model of the patient's upper jaw,
    a mandible member corresponding to a model of the patient's mandible, and movement means connected to said mandible member allowing six degrees of freedom of motion of the said mandible member relative to said upper jaw member,
    said movement means comprising six servo motors, each of said servo motors being connected to said mandible member for executing a single translation or rotation relative thereto, said servo motors comprising a first servo motor for movement along a first axis of translation, a second servo motor for movement along a second axis of translation, a third servo motor for movement along a third axis of translation, a fourth servo motor for movement about a first axis of rotation, a fifth servo motor for movement about a second axis of rotation, and a sixth servo motor for movement about a third axis of rotation, a base on which are mounted said six servo motors, said first servo motor being connected to said base and driving a carriage for translation in an X direction, said carriage being connected for movement along a pair of rails extending in the X direction which are fixed to said base, a pair of guides fixed to said carriage and extending in the Y direction, and a second carriage mounted thereon for movement by said second servo motor, a pair of further guides mounted on said second carriage and extending vertically, and a third carriage mounted on said further guides for movement vertically along said second guides, a fourth servo motor connected for rotation relative to said third carriage for rotation about the X axis, the fifth servo motor connected to said fourth servo motor, and adapted to rotate a shaft about the Z axis, and a sixth servo motor connected to said fifth servo motor and adapted to rotate said lower jaw member about said Y axis.

* * * * *